United States Patent [19]
Lehto

[11] Patent Number: 4,991,424
[45] Date of Patent: Feb. 12, 1991

[54] INTEGRATED HEATABLE SENSOR

[75] Inventor: Ari Lehto, Helsinki, Finland

[73] Assignees: Vaisala Oy, Helsinki; Kemira Oy, Espoo; Neste Oy, Espoo; Outokumpu Oy, Espoo, all of Finland; Engicom N.V., Boechout, Belgium

[21] Appl. No.: 355,283

[22] Filed: May 22, 1989

[30] Foreign Application Priority Data

Jun. 8, 1988 [FI] Finland ............................... 882697

[51] Int. Cl.⁵ ............................................. G01N 27/12
[52] U.S. Cl. ............................... 73/31.060; 73/25.050
[58] Field of Search ...................... 73/23, 25, 26, 27 R; 422/88, 94, 83, 95; 338/34

[56] References Cited

U.S. PATENT DOCUMENTS

| | | | |
|---|---|---|---|
| 4,338,281 | 7/1982 | Treitinger et al. | 73/31.06 X |
| 4,377,944 | 3/1983 | Hishii et al. | 73/31.06 |
| 4,580,439 | 4/1986 | Manaka | 73/31.06 |
| 4,674,319 | 6/1987 | Muller et al. | 73/31.06 X |

FOREIGN PATENT DOCUMENTS 2826515 1/1979 Fed. Rep. of Germany .
172948 7/1988 Japan .
184049 7/1988 Japan .

Primary Examiner—Hezron E. Williams
Assistant Examiner—Joseph W. Roskos

[57] ABSTRACT

The invention concerns a sensor construction for, e.g., the measurement of gas concentration, including a sensor element; a heating element arranged in conjunction with the sensor, with which the sensor element can be brought to a temperature above the ambient gas atmosphere temperature; and an electronics circuitry section, with which the desired electrical properties of the sensor element can be measured and the heating element of the sensor can be controlled. According to the invention, the sensor element and the electronics circuitry are placed onto the same planar substrate, and the substrate is processed to have adjacent openings around the sensor element area to the immediate vicinity of the area so that the openings extend through the substrate whereby the sensor area is connected to the surrounding part of the substrate and, then, to the electronics circuitry section, only along thin isthmuses remaining between the openings.

16 Claims, 2 Drawing Sheets

4,991,424

INTEGRATED HEATABLE SENSOR

BACKGROUND OF THE INVENTION

1. Field of the Invention

The present invention relates to an integrated heatable sensor for the purpose of measuring gas concentration.

Concentration measurements for different types of gases are performed in an increasing amount for both the living environment of man and industrial processes. Inflammable gases can be measured using sensors, which are operated with their surface temperature elevated above the ambient temperature. Inflammable gases in the ambient air are thereby oxidized on the sensor surface, and electrons released in the oxidization process alter the electrical conductivity of the sensor. Conventionally, this change in sensor resistance is converted into a voltage or current, whose magnitude is proportional to the gas concentration being measured.

2. Prior Art

In prior art constructions, the sensors are usually fabricated as separated sensor elements (or chips), which are bonded by electrical leads to the case encapsulating the sensor. In addition, the bonding leads act as springs, which support the sensor. Another method is to mount the sensor onto heat-insulating posts, while the electrical connections are bonded with thin conductors leads.

The first mentioned construction has two principal drawbacks. Firstly, the spring leads must be designed with a sufficient thickness in order to provide protection for the sensor against mechanical stresses, e.g., those caused by impact shocks. By contrast, a thicker lead conducts a great deal of heat away from the sensor element to thereby necessitate the application of increased heating power. Secondly, although mass production methods are being applied in the processing of the sensors, their fabrication into separated chips, the individual mounting of the chips into the sensor case, and the bonding of the chips to the attached electronics results in a complicated and expensive sensor manufacturing process.

SUMMARY OF THE INVENTION

The aim of the present invention is to overcome the disadvantages of the above described prior art technology and achieve a totally new kind of integrated heatable sensor.

The invention is based on integrating the sensor element onto the same substrate with the electronics circuitry and, further, heat-insulating it from the rest of the substrate by means of openings fabricated around the sensor area.

More specifically, the integrated heatable sensor in accordance with the invention is characterized in that it is placed on a common substrate with the electronics circuitry and the substrate is formed with adjacent openings situated around the sensor element which extend through the substrate.

The construction in accordance with the invention provides outstanding benefits.

The invention makes it possible to integrate a heatable sensor onto, e.g., the substrate of a thick-film hybrid circuit so that the sensor and the substrate form such an integrated structure in which the heat flow from the sensor to the substrate is minimized. The sensor can be integrated onto a substrate containing the electronics circuitry during a single workphase in the mass production process. Further, an advantageous method such as laser processing can be applied to the fabrication of the openings by virtue of combining this workphase with that of the thick-film resistor trimming operation performed during the calibration of the sensors.

BRIEF DESCRIPTION OF THE DRAWINGS

The invention is next examined in detail with help of the following exemplifying embodiments illustrated in the attached figures which are given by way of illustration only, and thus are not limitative of the present invention, and wherein.

DETAILED DESCRIPTION OF THE PREFERRED EMBODIMENTS

With reference to the production methods of thick-film and thin-film hybrid circuits explicitly described in, e.g., such publications as Hammer D. W., Biggers J. V., Thick Film Hybrid Microcircuit Technology, Wiley-Interscience 1972, and Holmes P. J., Handbook of Thick Film Technology, Electrochemical Publications Ltd., 1976, the details of the aforementioned techniques are omitted herein.

Figure 1:
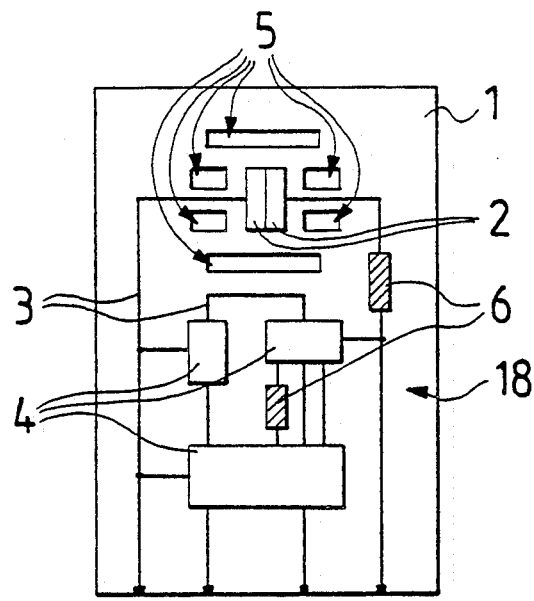
FIG. 1 is a top view of an integrated sensor construction in accordance with an embodiment of the present invention.

According to FIG. 1, a tin-oxide based sensor 2 is fabricated onto, e.g., an alumina substrate 1 in a conventional manner, while an additional workphase is also performed by simultaneously fabricating lead connections 3 of surface-mount electronical components 4 as well as resistors 6. The heating resistor of the sensor 2 may be placed on either the lower or the upper surface of the substrate. In the construction illustrated in FIG. 1, the heating resistor is placed outside the illustrated area, under the sensor 2. In conjunction with the bonding of the surface-mount components 4, openings 5 are fabricated around the sensor area at appropriate places using, e.g., a laser. These openings 5 isolate the sensor 2 thermally from the rest of the substrate. A typical size of the sensor is a few square millimeters and the size of the substrate is, e.g., 2-3 cm$^2$. The width of the cut openings 5 can be, e.g., a few hundred micrometers.

Figure 2:
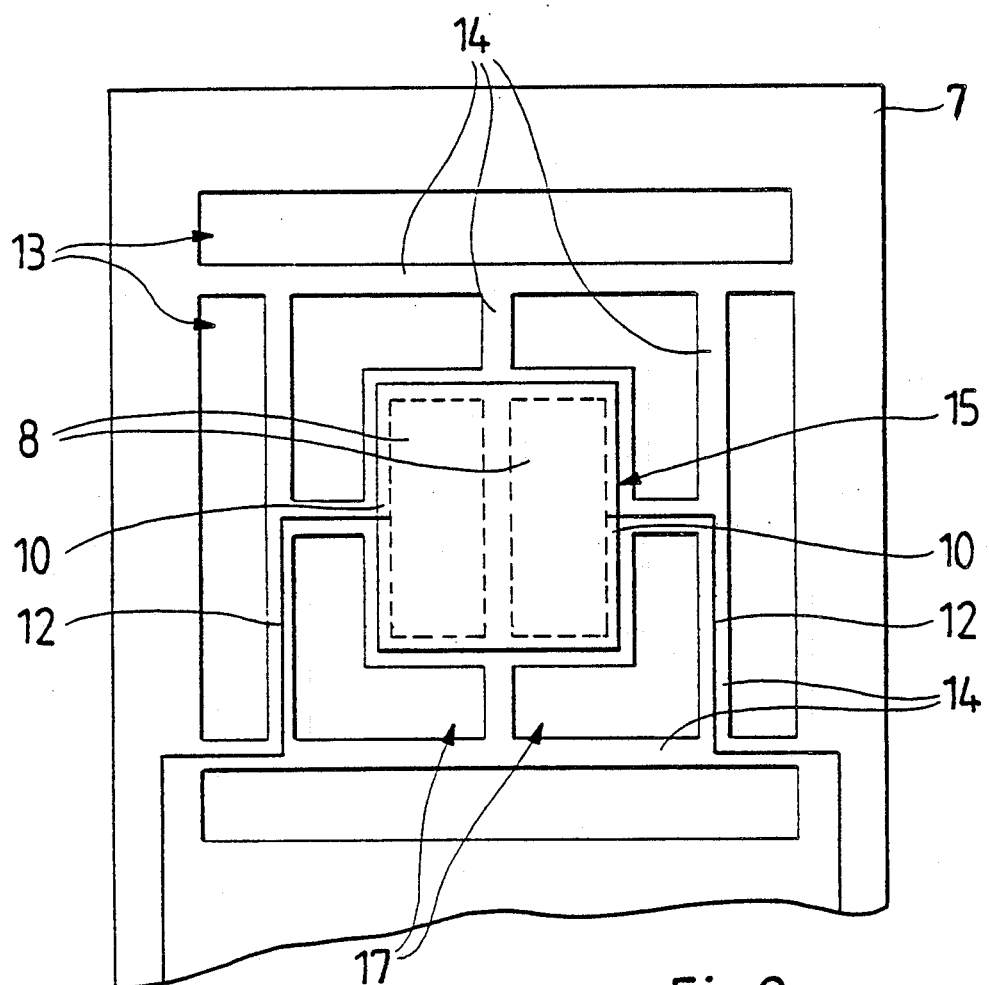
FIG. 2 is a top view of another integrated sensor construction in accordance with a further embodiment of the present invention.

In accordance with FIG. 2, metal electrodes 8 and conductors 12 are processed onto a substrate 7 using thick-film or thin-film techniques. A gas-sensitive layer 10 of appropriate sensor material, e.g., $SnO_2$ is sintered onto the electrodes 8. The entity called here a sensor 15 is defined to include a sensor material layer 10 and the electrodes 8. In the construction illustrated in FIG. 2, the openings are arranged so that the sensor 15 is surrounded by an annular first set of inner openings, consisting of four L-shaped openings 17, which are further enclosed by a second set of outer openings, consisting of four rectangular openings 13. Conductors 12 of the electrodes 8 are routed via isthmuses 14 remaining between the openings 13 and 17. The ratio of the isthmuses to the circumference of the sensor 15 is about 10%, but this parameter may be varied from 5% to 15% as dictated by the material type and other needs. The electronic circuitry, together with its associated components, is not illustrated in FIG. 2; however, its location is outlined in FIG. 1.

Figure 3:
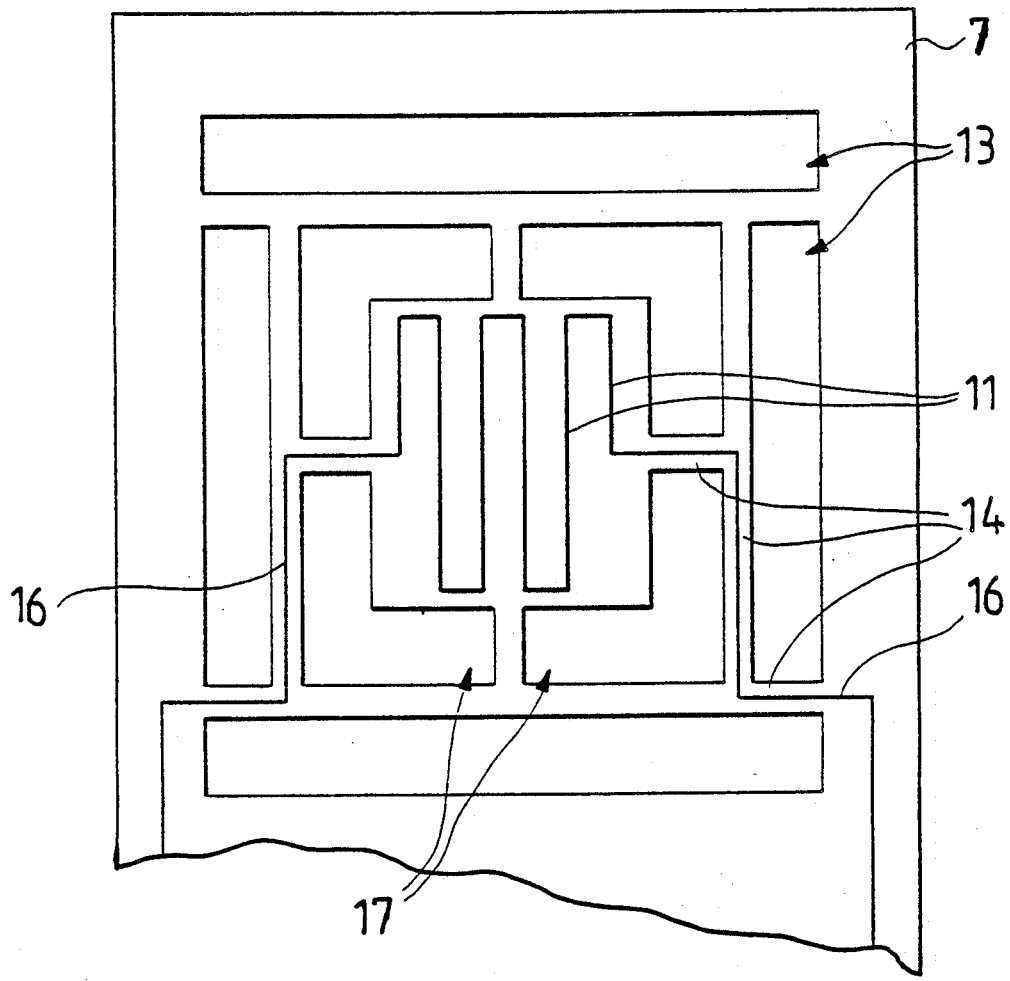
FIG. 3 is a bottom view of the sensor construction illustrated in FIG. 2.

Illustrated in FIG. 3 is the placement of a heating resistor 11 of the sensor to the bottom side of the substrate 7. Conductors 16 of the heating resistor are routed to the substrate along isthmuses remaining between openings 13 and 14.

The shape of the openings may obviously vary within very large limits, since the most advantageous tool, the laser, offers an extremely wide latitude of control. Hence, the proposed rectangular shapes of openings can feasibly be replaced by freely selected shapes with curved contours. Furthermore, the ideally circular shape can be replaced by an elliptic contour.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. An integrated sensing apparatus for measuring gas concentration comprising:
   a sensor element for providing a sensor signal;
   a heating element arranged in conjunction with the sensor element for heating the sensor element to a temperature above the ambient gas atmosphere temperature; and
   electronic circuitry, coupled to the sensor element and the heating element, for measuring desired electrical properties of the sensor element in accordance with the sensor signal and controlling the heating element in response thereto,
   the sensor element and the electronic circuitry being placed on a common planar substrate, and that
   the common planar substrate including adjacent openings situated around the sensor element in the immediate vicinity thereof and extending entirely through the common planar substrate such that only thin isthmuses are formed between the adjacent openings for connecting the sensor element to the surrounding part of the common planar substrate and to the electronic circuitry.

2. The integrated sensing apparatus as claimed in claim 1, wherein the sensor element (8, 10) and the electronic circuitry are thick-film devices formed on said substrate.

3. The integrated sensing apparatus as claimed in claim 1, wherein the sensor element and the electronic circuitry are thin-film devices formed on said substrate.

4. The integrated sensing apparatus as claimed in claim 1, wherein the heating element is placed on a bottom surface of the common planar substrate in alignment with the sensor element.

5. The integrated sensing apparatus as claimed in claim 1, wherein the adjacent openings are comprised of two sets of openings, which coaxially and annularly enclose the sensor element.

6. The integrated sensing apparatus as claimed in claim 1, wherein the sensor element is attached to the surrounding part of the common planar substrate along the thin isthmuses whereby the isthmus to sensor circumference ratio is within a range of 5-15%.

7. The integrated sensing element of claim 6 wherein said isthmus to sensor circumference ratio is about 10%.

8. The integrated gas sensor of claim 1 wherein said openings are laser formed openings.

9. An integrated gas sensor formed on an upper surface of a substrate comprising:
   sensor means for providing a sensor signal;
   heating means, proximate to said sensor means, for heating said sensor means;
   electronic circuitry, coupled to said sensor means and said heating means, for measuring desired electrical properties of said sensor means in accordance with said sensor signal and for controlling said heating means; and
   means for thermally isolating said sensor means and said heating means from said electronic circuitry, said means for thermally isolating including a plurality of openings proximate said sensor means and formed entirely through said substrate.

10. The integrated gas sensor of claim 9 further comprising a plurality of thin isthmuses between said openings, said isthmus facilitating the electrical connection of said electronic circuitry to said sensor means via conductors along said thin isthmuses.

11. The integrated gas sensor of claim 10 wherein the ratio of thin isthmuses to sensor means circumference is in the range of 5-15%.

12. The integrated gas sensor of claim 11 wherein the ratio of thin isthmuses to sensor means circumference is about 10%.

13. The integrated gas sensor of claim 10 wherein said heating means is placed on a bottom surface of said substrate in alignment with said sensor means.

14. The integrated gas sensor of claim 10 wherein said sensor means and said electronic circuitry are thin-film devices.

15. The integrated gas sensor of claim 10 wherein said sensor means and said electronic circuitry are thick-film devices.

16. The integrated gas sensor of claim 10 wherein said openings are comprised of two sets of openings, a first set coaxially and a second set of annularly proximate to said sensor means.

* * * * *